United States Patent
Choi

(10) Patent No.: US 11,457,858 B2
(45) Date of Patent: Oct. 4, 2022

(54) SKIN DIAGNOSTIC DEVICE AND COUPLING SYSTEM THEREFOR

(71) Applicant: CHOWIS CO., LTD., Yongin-si (KR)

(72) Inventor: Won Suk Choi, Yongin-si (KR)

(73) Assignee: CHOWIS CO., LTD., Gyeonggi-Do (KR)

( * ) Notice: Subject to any disclaimer, the term of this patent is extended or adjusted under 35 U.S.C. 154(b) by 442 days.

(21) Appl. No.: 16/665,321

(22) Filed: Oct. 28, 2019

(65) Prior Publication Data
US 2020/0060608 A1   Feb. 27, 2020

Related U.S. Application Data

(63) Continuation of application No. PCT/KR2018/011457, filed on Sep. 27, 2018.

(30) Foreign Application Priority Data

Sep. 28, 2017   (KR) .................. 10-2017-0126347

(51) Int. Cl.
*A61B 5/00* (2006.01)

(52) U.S. Cl.
CPC ............ *A61B 5/441* (2013.01); *A61B 5/0077* (2013.01)

(58) Field of Classification Search
CPC ............................... A61B 5/0077; A61B 5/05
USPC ......................................................... 600/306
See application file for complete search history.

(56) References Cited

U.S. PATENT DOCUMENTS

| 2004/0190239 | A1 | 9/2004 | Weng et al. | |
| 2012/0268648 | A1* | 10/2012 | Yang | G02B 7/102 348/360 |
| 2013/0127309 | A1* | 5/2013 | Wyner | G03B 17/08 312/223.1 |
| 2014/0119718 | A1* | 5/2014 | Oh | G03B 11/041 396/448 |

(Continued)

FOREIGN PATENT DOCUMENTS

| KR | 20-0297234 Y1 | 12/2002 |
| KR | 20-0418806 Y1 | 6/2006 |
| KR | 10-2007-0010336 A | 1/2007 |

(Continued)

OTHER PUBLICATIONS

Office Action for corresponding Korean application 10-2018-0153940 dated Nov. 20, 2020, 6 pgs., with English machine translation.

(Continued)

*Primary Examiner* — Fabricio R Murillo Garcia
(74) *Attorney, Agent, or Firm* — Crowell & Moring, L.L.P.

(57) ABSTRACT

A skin diagnostic device is provided that includes a body including a coupling member positioned on one surface, the body being attached/detached to/from an electronic device including an image sensor by using the coupling member, an optical unit positioned in the body and including at least one lens, wherein the optical unit is configured to focus measurement light reflected from a target on the image sensor of the electronic device, and at least one light source unit positioned adjacent to the optical unit and configured to irradiate light toward the target, wherein the coupling member includes at least one magnetic body and an alignment member positioned adjacent to the magnetic body.

11 Claims, 12 Drawing Sheets

(56) References Cited

U.S. PATENT DOCUMENTS

2017/0303857 A1* 10/2017 Perkins ................ A61B 1/303

FOREIGN PATENT DOCUMENTS

| KR | 10-0781235 B1 | 11/2007 |
| KR | 10-2011-0100999 A | 9/2011 |
| KR | 10-1425203 B1 | 8/2014 |
| KR | 10-2017-0093645 A | 8/2017 |

OTHER PUBLICATIONS

First Office Action for Korean Patent Application No. 10-2017-0126347 dated Jan. 10, 2018; 4 pages.
Second Office Action for Korean Patent Application No. 10-2017-0126347 dated May 1, 2018; 4 pages.
International Search Report and Written Opinion with English Translation for International Application No. PCT/KR2018/011457 dated Jan. 14, 2019; 11 pages.

* cited by examiner

SKIN DIAGNOSTIC DEVICE AND COUPLING SYSTEM THEREFOR

CROSS-REFERENCE TO RELATED APPLICATION(S)

This application is a bypass continuation of International Patent Application No. PCT/KR2018/011457, filed Sep. 27, 2018, which claims priority to Korean Patent Application No. 10-2017-0126347, filed on Sep. 28, 2017, the entirety of all of which are hereby incorporated by reference herein.

TECHNICAL FIELD

Embodiments of the disclosure relate to a skin diagnostic device and a coupling system therefor.

BACKGROUND

With an increase in life expectancy, a diagnosis and management of physical conditions became one of essential matters. The skin, on which a human body is exposed to external environments, includes various metabolites and components, and in some cases, the skin serves as an indicator representing physical conditions. As a concrete example, when a human has a bad complexion, bad circulation or digestion is suspected. As another example, when skin troubles occur, mental stress is suspected.

Typically, a diagnosis of a skin condition has been performed, mainly, by a visual or tactile method. Specifically, skin elasticity is visually determined through an optical microscope, and skin water content is tactually determined. However, the determination methods have low accuracy, and in many cases, determinations depend on a human's experience.

Meanwhile, skin monitoring for diagnosing physical conditions needs to be done regularly. Accordingly, a skin condition diagnostic device and method capable of performing monitoring and diagnosis more easily without giving unpleasant feelings to examinees are required. Recently, a trial for irradiating light onto the skin, photographing the skin, and then analyzing information of the light to examine a skin condition is being conducted. However, because most diagnostic equipment for such a diagnosis is high-priced, the diagnostic equipment is used mainly in skin-related businesses, such as skin care shops or dermatology hospitals.

DESCRIPTION OF EMBODIMENTS

Technical Problem

Embodiments of the disclosure aim to provide a skin diagnostic device which is portable and capable of improving the accuracy of a position of an optical unit with respect to an image sensor of an electronic device, and a coupling system for the skin diagnostic device.

Solution to Technical Problem

An embodiment of the disclosure provides a skin diagnostic device including: a body including a coupling member positioned on one surface, the body being attached/detached to/from an electronic device including an image sensor by using the coupling member; an optical unit positioned in the body and including at least one lens, wherein the optical unit is configured to focus measurement light reflected from a target on the image sensor of the electronic device; and at least one light source unit positioned adjacent to the optical unit and configured to irradiate light toward the target, wherein the coupling member may include at least one magnetic body and an alignment member positioned adjacent to the magnetic body.

Advantageous Effects

Because a skin diagnostic device according to embodiments of the disclosure is coupled with an electronic device by using coupling members including magnetic bodies with different polarities, an optical unit of the skin diagnostic device may be located precisely at an image sensor of the electronic device. Therefore, a user may measure a skin condition under the same condition at any time so that an accurate skin diagnosis may be possible.

Also, because the skin diagnostic device according to the embodiments of the disclosure further includes a sensor unit for measuring an amount of moisture in the skin, the skin diagnostic device may acquire more information for a skin diagnosis. Particularly, because a measurement direction of the sensor unit is different from a measurement direction of the image sensor in the skin diagnostic device, a user may more conveniently use the sensor unit to measure the skin.

Also, because the skin diagnostic device according to the embodiments of the disclosure further includes a light guide member for focusing light entering from a light source unit on the skin, the skin diagnostic device may acquire a clear, accurate skin measurement image.

DETAILED DESCRIPTION

Figure 1:
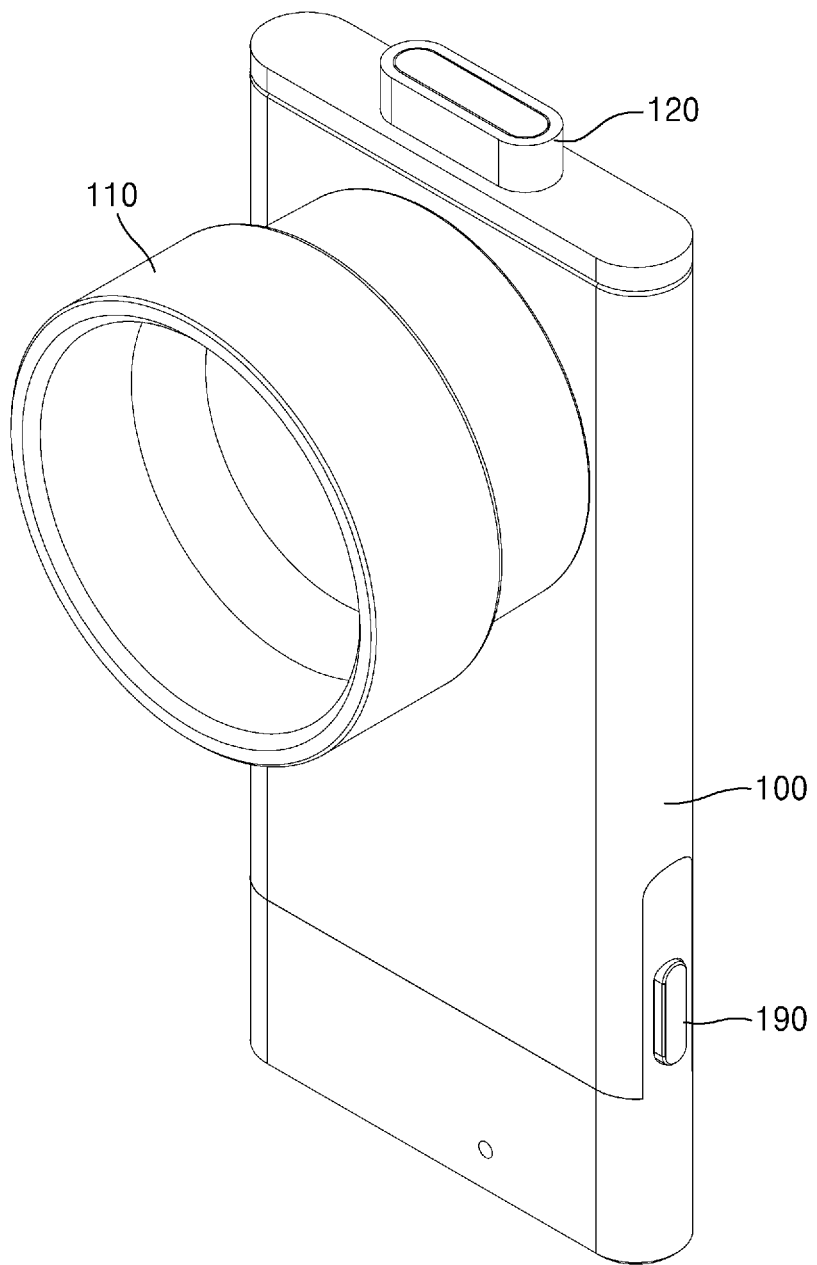
FIG. 1 is a perspective view of a skin diagnostic device according to an embodiment of the disclosure.

An embodiment of the disclosure provides a skin diagnostic device including: a body including a coupling member positioned on one surface, the body being attached/detached to/from an electronic device including an image sensor by using the coupling member; an optical unit positioned in the body and including at least one lens, wherein the optical unit is configured to focus measurement light reflected from a target on the image sensor of the electronic device; and at least one light source unit positioned adjacent to the optical unit and configured to irradiate light toward the target, wherein the coupling member may include at least one magnetic body and an alignment member positioned adjacent to the magnetic body.

According to an embodiment of the disclosure, the magnetic body may be positioned on the same line as the optical unit.

According to an embodiment of the disclosure, the skin diagnostic device may further include a sensor unit positioned on the other surface of the body, not on the one surface of the body, and including a moisture sensor configured to measure an amount of moisture in the target.

According to an embodiment of the disclosure, the skin diagnostic device may further include a sensor unit including a moisture sensor configured to measure an amount of moisture in the target, wherein a first imaginary line passing the image sensor and the optical unit may cross a second imaginary line passing a measurement surface of the sensor unit.

According to an embodiment of the disclosure, the skin diagnostic device may further include a supporter including one end positioned on the other surface of the body, the other surface being opposite to the one surface of the body, wherein an opening penetrating the one end and the other end being opposite to the one end may be formed in the supporter.

According to an embodiment of the disclosure, the supporter may further include a light guide member positioned on a path of light irradiated from the light source unit and configured to change a path of at least one part of the light irradiated from the light source unit to focus the light on the other end of the supporter.

According to an embodiment of the disclosure, the light source unit may include a plurality of light sources spaced at regular intervals while surrounding the optical unit.

One or more embodiments provide a coupling system for a skin diagnostic device, including: a first coupling member including a first surface and a second surface that is opposite to the first surface and including at least one magnetic body positioned on the first surface and a first alignment member positioned adjacent to the magnetic body; and a second coupling member including a third surface that is opposite to the first surface and a fourth surface that is opposite to the third surface and including at least one magnetic body positioned on the third surface and a second alignment member positioned adjacent to the magnetic body and aligned with the first alignment member.

According to an embodiment of the disclosure, the coupling system may further include an electronic device including the first coupling member and an image sensor; and a skin diagnostic device including a body including the second coupling member positioned on one surface, the body being attached/detached to/from the electronic device by using the second coupling member; an optical unit positioned in the body and including at least one lens, wherein the optical unit is configured to focus measurement light reflected from a target on the image sensor of the electronic device; and at least one light source unit positioned adjacent to the optical unit and configured to irradiate light toward the target, wherein the magnetic body of the second coupling member may be positioned on the same line as the optical unit.

According to an embodiment of the disclosure, the skin diagnostic device may further include a sensor unit positioned on the other surface of the body, not on the one surface of the body, and including a moisture sensor configured to measure an amount of moisture in the target.

According to an embodiment of the disclosure, the skin diagnostic device may further include a sensor unit including a moisture sensor configured to measure an amount of moisture in the target, wherein a first imaginary line passing the image sensor and the optical unit may cross a second imaginary line passing a measurement surface of the sensor unit.

According to an embodiment of the disclosure, the skin diagnostic device may further include a supporter including one end positioned on the other surface of the body, the other surface being opposite to the one surface of the body, wherein an opening penetrating the one end and the other end being opposite to the one end may be formed in the supporter.

According to an embodiment of the disclosure, the supporter may further include a light guide member positioned on a path of light irradiated from the light source unit and configured to change a path of at least one part of the light irradiated from the light source unit to focus the light on the other end of the supporter.

Other aspects, features, advantages than the above description will be apparent from the following drawings, claims, and the detailed description.

Hereinafter, the embodiments of the disclosure will be described in detail with reference to the accompanying drawings. Also, the same or corresponding components in the following description with reference to the drawings will be assigned the same reference numerals, and overlapping descriptions thereof will be omitted.

While the embodiments are susceptible to various modifications, specific embodiments thereof are shown by way of example in the drawings and will herein be described in detail. Advantages and features of the embodiments and a method of achieving the advantages and features will be apparent by referring to detailed descriptions given below in connection with the accompanying drawings. However, the embodiments of the disclosure are not limited to the following embodiments, and may be implemented in various forms.

In the following embodiments, it will be understood that, although the terms "first", "second", etc. may be used herein to describe various components, these components should not be limited by these terms. These terms are only used to distinguish one component from another.

In the following embodiments, it will be understood that the singular forms "a," "an," and "the" include plural referents unless the context clearly dictates otherwise.

In the following embodiments, it will be understood that the terms "comprises", "may comprise,", "includes" and/or "may include", when used herein, specify the presence of features or components written in this specification, but do not preclude the presence or addition of one or more other features or components.

In the following embodiments, it will also be understood that when a portion, such as a unit, a region, a component, etc., is referred to as being "on" or "above" another portion, it can be directly on the other portion, or an intervening unit, region, component, etc. may also be present.

In the following embodiments, the terms "connected" or "coupled" does not necessarily mean a direct and/or fixed connection or coupling between two members unless the context clearly dictates otherwise, and another intervening member may exist between the two members.

In the drawings, for convenience of description, the sizes of components are more or less exaggeratedly shown. For example, the sizes and thicknesses of the components shown in the drawings are arbitrarily represented for convenience of description, and the following embodiments are not limited to the sizes and thicknesses.

Hereinafter, a skin diagnostic device according to an embodiment of the disclosure and a coupling system therefor will be described with reference to the accompanying drawings.

Figure 2:
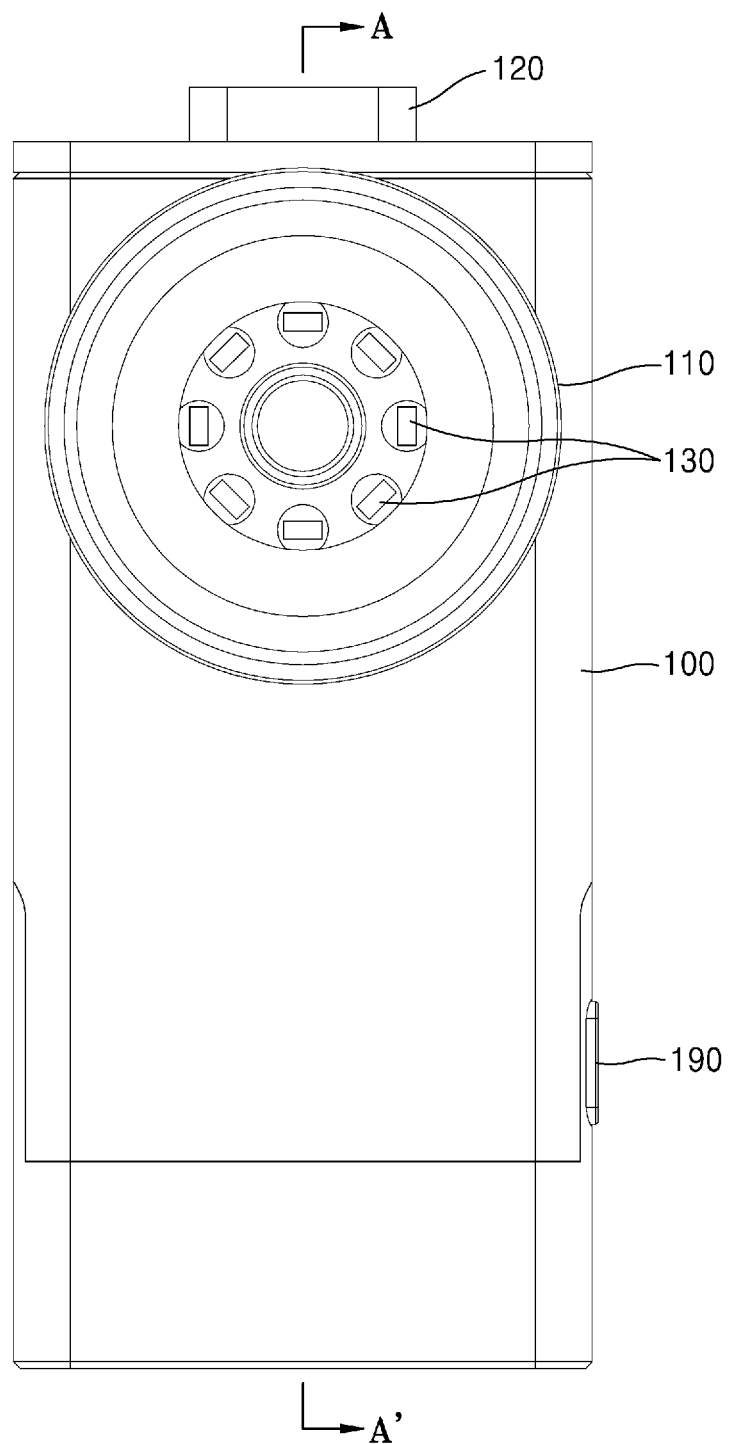
FIG. 2 is a front view of the skin diagnostic device shown in FIG. 1.
Figure 3:
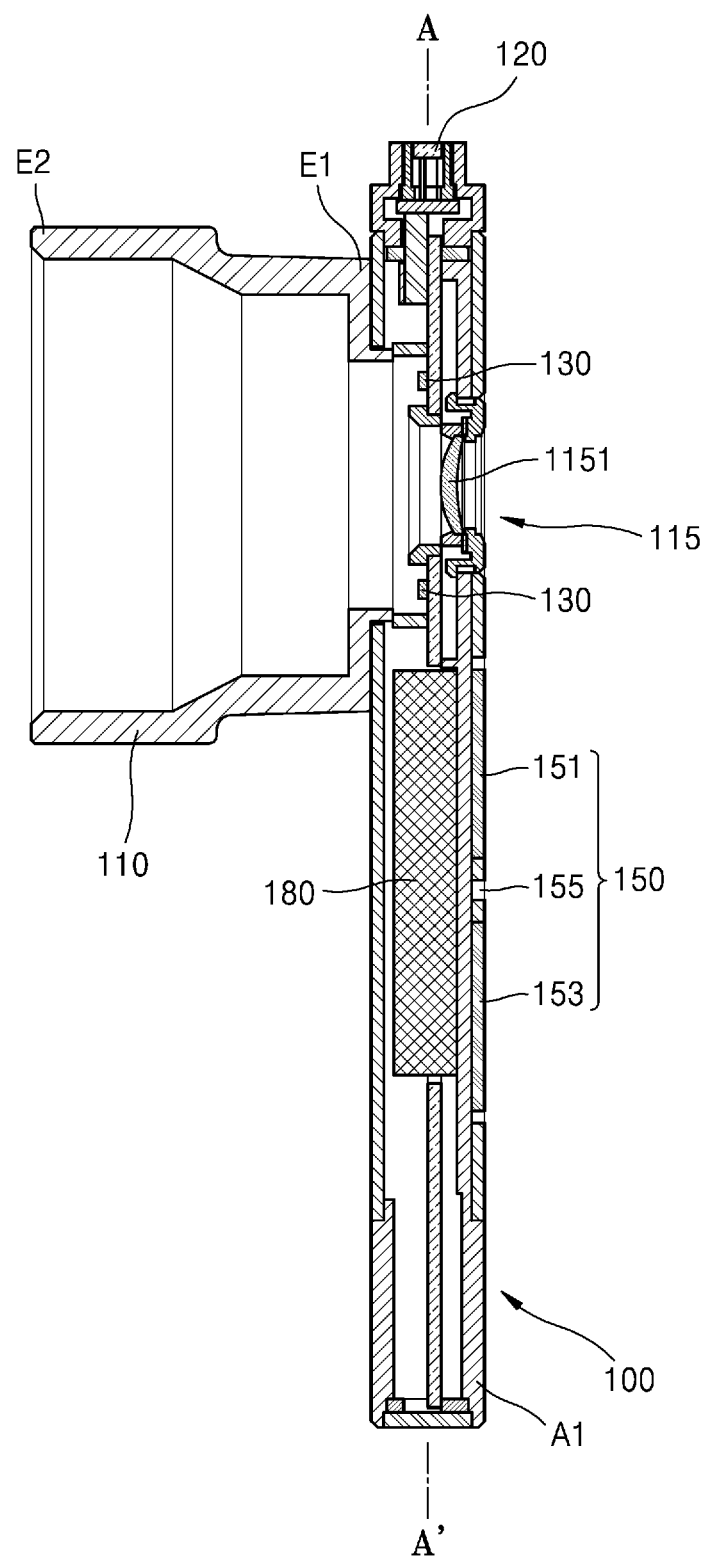
FIG. 3 is a cross-sectional view of the skin diagnostic device shown in FIG. 2, taken along line A-A'.
Figure 4:
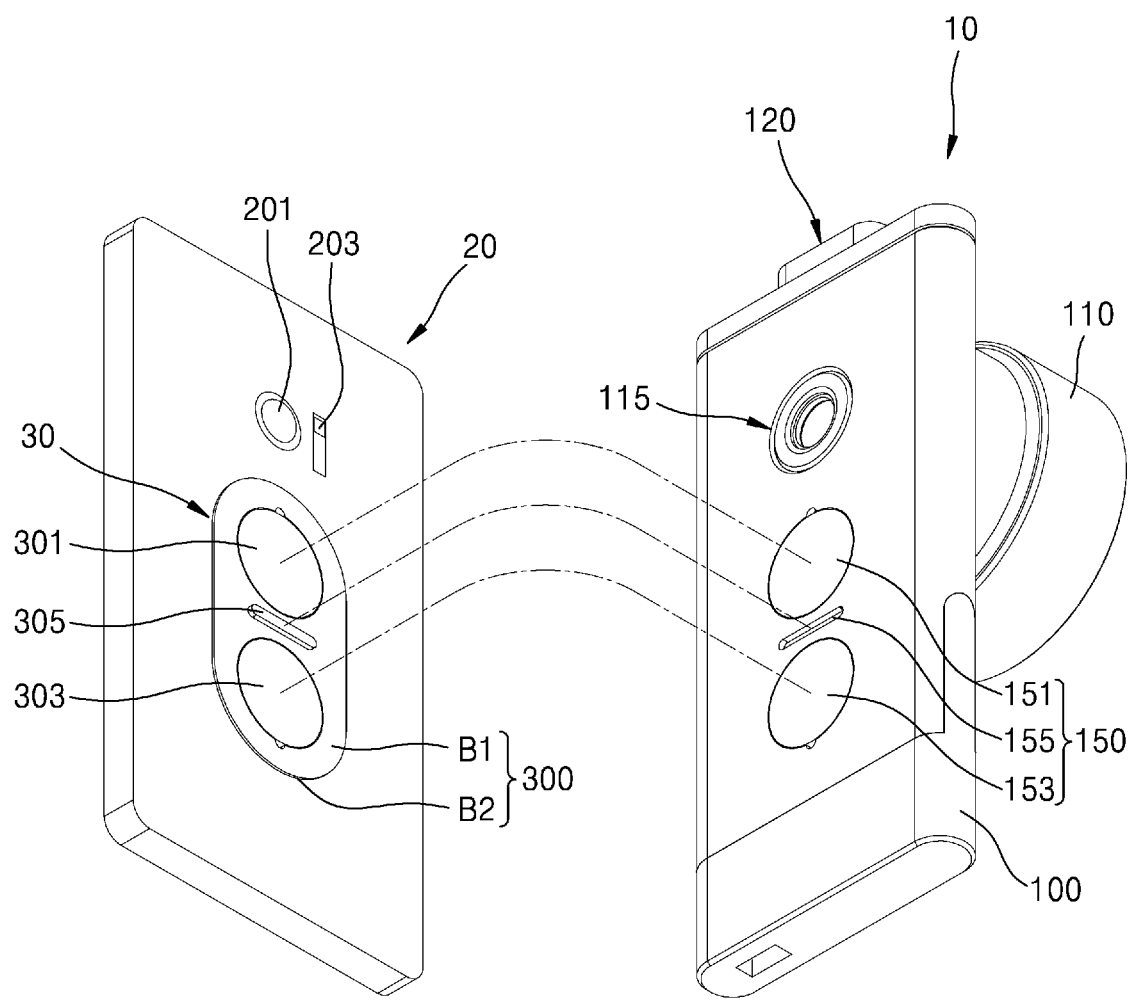
FIG. 4 schematically shows a coupling system for a skin diagnostic device according to an embodiment of the disclosure.
Figure 5:
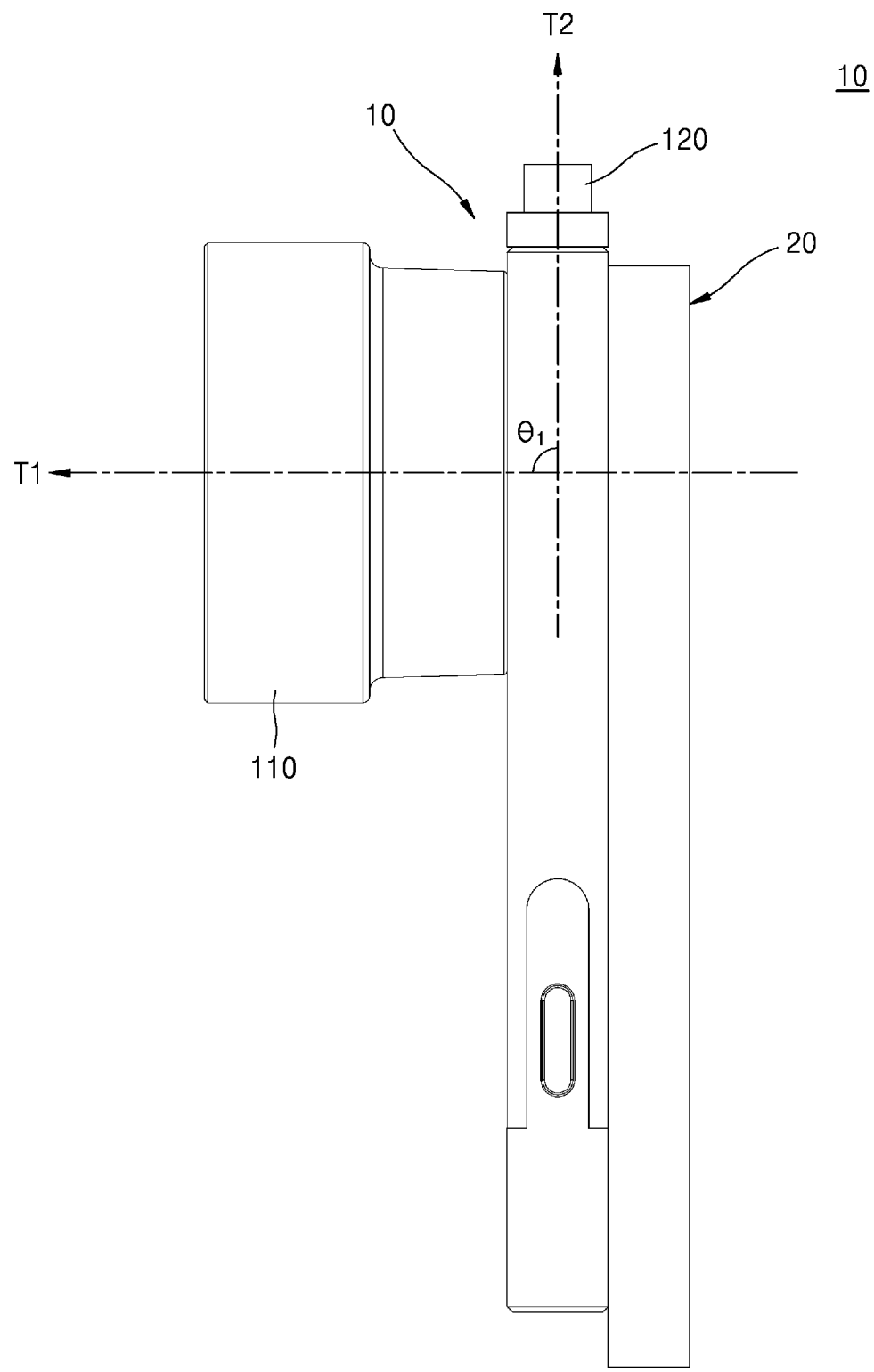
FIG. 5 is a side view showing a state in which the skin diagnostic device shown in FIG. 4 is coupled with an electronic device.
Figure 6:
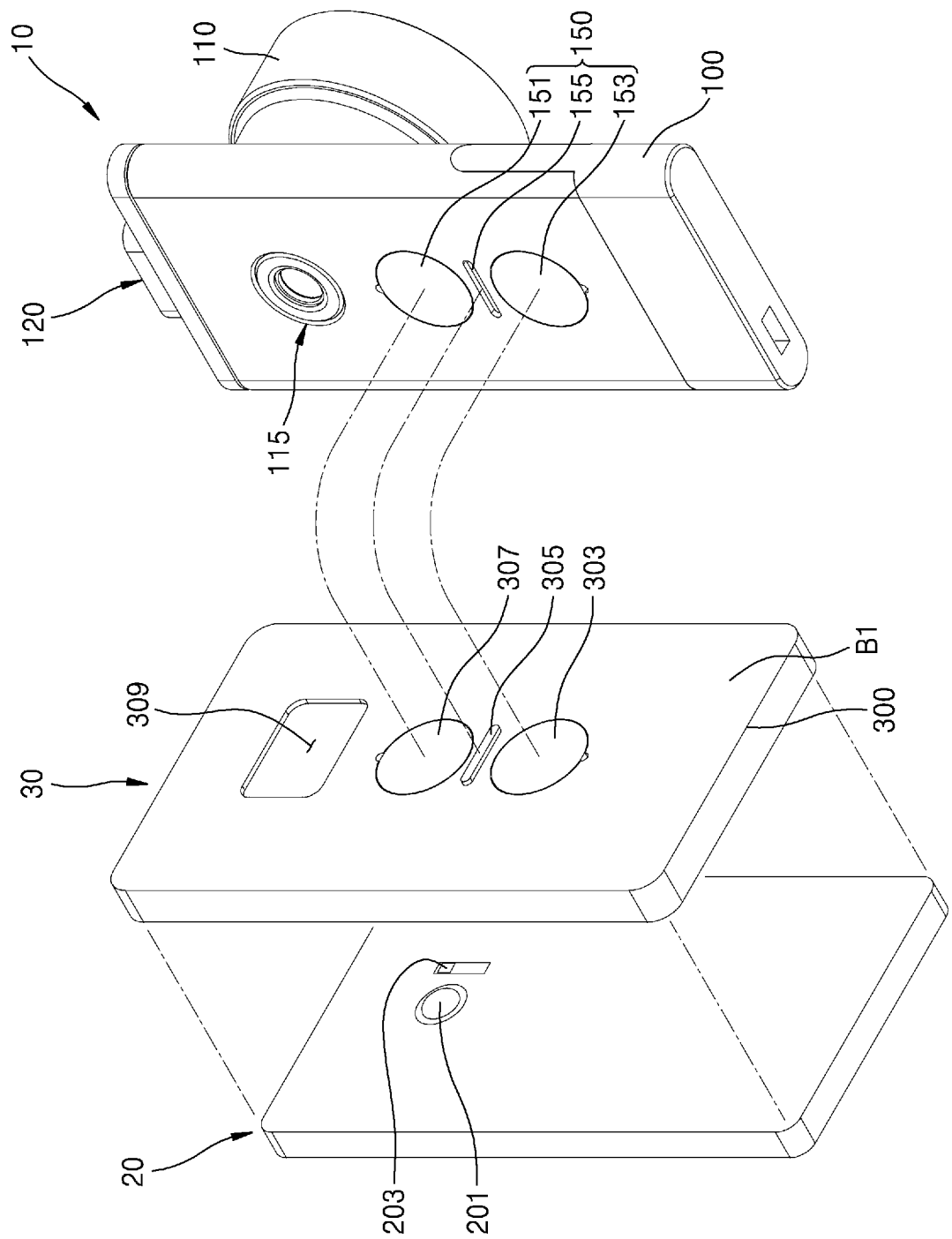
FIG. 6 shows another embodiment in which the skin diagnostic device shown in FIG. 4 is coupled with an electronic device.

FIG. 1 is a perspective view of a skin diagnostic device 10 according to an embodiment of the disclosure, FIG. 2 is a front view of the skin diagnostic device 10 shown in FIG. 1, and FIG. 3 is a cross-sectional view of the skin diagnostic device 10 shown in FIG. 2, taken along line A-A'. FIG. 4 schematically shows a coupling system 1 for a skin diagnostic device according to an embodiment of the disclosure, and FIG. 5 is a side view showing a state in which the skin diagnostic device 10 shown in FIG. 4 is coupled with an electronic device 20. FIG. 6 shows another embodiment in which the skin diagnostic device 10 shown in FIG. 4 is coupled with the electronic device 20.

Referring to FIGS. 1 to 6, the skin diagnostic device 10 according to an embodiment of the disclosure may include a body 100, an optical unit 115, and at least one light source unit 130, and further include a sensor unit 120 and a supporter 110.

The body 100 may include a second coupling member 150 positioned on one surface. The body 100 may be attached/detached to/from the electronic device 20 including an image sensor 201 through the second coupling member 150. According to an embodiment, the body 100 may form an outer appearance of the skin diagnostic device 10, and accommodate a component such as a power supply 180 (e.g., battery) through a cavity formed in the inside. The body 100 may be manufactured in a compact size to be carried.

Herein, the electronic device 20 may include the image sensor 201 positioned on one surface, and further include a lighting unit 203. The electronic device 20 may include a display (not shown), and the one surface may be opposite to a surface on which the display (not shown) is positioned. According to another embodiment, the one surface may be the surface on which the display (not shown) is positioned. According to another embodiment, the electronic device 20 may include two or more image sensors 201, wherein the image sensors 201 may be respectively positioned on the surface on which the display is positioned and the opposite surface. For example, the electronic device 20 may be a mobile phone, a tablet, a notebook, a graphing calculator, a portable game, a digital camera, a digital camcorder, a portable media player, or the like.

The second coupling member 150 positioned on one surface of the body 100 may include at least one magnetic body. According to an embodiment, the magnetic body may include a first magnetic body 151 and a second magnetic body 153 spaced from the first magnetic body 151. The first magnetic body 151 and the second magnetic body 153 may have different polarities. For example, when the first magnetic body 151 is a N pole, the second magnetic body 153 may be a S pole, and when the first magnetic body 151 is a S pole, the second magnetic body 153 may be a N pole. The second coupling member 150 may locate the optical unit 115 precisely at the image sensor 201 by coupling the first magnetic body 151 and the second magnetic body 153, respectively, with a third magnetic body 301 and a fourth magnetic body 303 of a first coupling member 30 which will be described later. Accordingly, the first magnetic body 151 and the second magnetic body 153 may be arranged to correspond to an arrangement of the third magnetic body 301 and the fourth magnetic body 303 and a distance between the third magnetic body 301 and the fourth magnetic body 303. However, the disclosure is not limited to this, and the magnetic body may be any one of the first magnetic body 151 and the second magnetic body 153. In this case, the first coupling member 30 may also include a single magnetic body to correspond to the magnetic body. Hereinafter, an embodiment in which the magnetic body includes the first magnetic body 151 and the second magnetic body 153 will be described.

According to an embodiment, the first magnetic body 151 and the second magnetic body 153 may be aligned on the same line as the optical unit 115. More specifically, a center of the first magnetic body 151 and a center of the second magnetic body 153 may be aligned on the same line as a center of the optical unit 115. However, the disclosure is not limited to this, and according to another embodiment, an imaginary extension line passing the center of the first magnetic body 151 and the center of the second magnetic body 153 may cross another imaginary extension line passing the center of the optical unit 115.

Meanwhile, as shown in FIG. 3, the second coupling member 150 may be a structure coupled with one surface A1 of the body 100, and the second coupling member 150 and the body 100 may be integrated into one body. According to another embodiment, the second coupling member 150 may be a structure separated from the body 100, and may be attached on one surface of the body 100.

The second coupling member 150 may further include a second alignment member 155 positioned adjacent to the magnetic body. The second alignment member 155 may include a groove or protrusion, and the groove or protrusion included in the second alignment member 155 may correspond to a groove or protrusion included in a first alignment member 305 which will be described later.

According to an embodiment, the second alignment member 155 may be positioned between the first magnetic body 151 and the second magnetic body 153. For example, the first alignment member 305 may be positioned between the third magnetic body 301 and the fourth magnetic body 303. When the first alignment member 305 includes a long straight-lined protrusion, the second alignment member 155 may include a long, straight-lined groove to accommodate the long straight-lined protrusion. Also, the second alignment member 155 may include at least one groove or protrusion. For example, the second alignment member 155 may include a single protrusion and a single groove. However, a shape of the second alignment member 155 is not limited to a straight-lined groove or protrusion. The second alignment member 155 may have any shape, such as a cross shape, a circle shape, a polygon shape, etc., as long as the second alignment member 155 is able to be coupled with the first alignment member 305 to help an alignment of the first coupling member 30 and the second coupling member 150.

The optical unit 115 may be positioned in the body 100 and include at least one lens 1151 to focus measurement light reflected from a target on the image sensor 201 of the electronic device 20. According to an embodiment, the optical unit 115 may include at least one lens for enlarging a surface image of a target. According to an embodiment, the optical unit 115 may include a wide angle lens and a macroscopic lens and include a fixing member for fixing the lenses. The optical unit 115 may enlarge a surface image of a target, in other words, a skin image, by using the wide angle lens and the macroscopic lens, and the optical unit 115 may be fixed at the body 100 to maintain a predetermined focal distance.

The light source unit 130 may be positioned adjacent to the optical unit 115 and irradiate light toward a target. For example, the light source unit 130 may be a plurality of light sources spaced at regular intervals while surrounding the optical unit 115. The light source unit 130, which is a light source used in a general electronic device such as a mobile phone, may be a light source having a wide wavelength band, for example, a light source that irradiates light of a full visible-light wavelength band. However, the disclosure is not limited to this, and the light source unit 130 may be a light source having a specific wavelength band.

For example, the light source unit 130 may irradiate light of a wavelength band required for diagnosing a skin condition. For example, coproporphyrin 3, which is one of porphyrin generated in the skin by propionibacterium acne (P. acne) of acne vulgaris, has an absorption spectrum with a peak of 407 nm. For example, when light of a blue light band (400 nm to 440 nm) is irradiated to the skin, porphyrin strongly absorbs energy of light of a blue wavelength band, and fluoresces light of a unique wavelength band that is different from the absorbed wavelength. By analyzing the absorption spectrum, a skin condition of a target may be diagnosed.

According to another embodiment, the light source unit 130 may include a plurality of light sources having different wavelength bands. In this case, the skin diagnostic device 10 may control the light source unit 130 to irradiate light through a light source of a wavelength band required for diagnosis according to a user's selection.

Meanwhile, the skin diagnostic device 10 according to an embodiment of the disclosure may further include the supporter 110 and the sensor unit 120.

One end E1 of the supporter 110 may be positioned on the other surface of the body 100, the other surface being opposite to the one surface A1 of the body 100, and an opening may penetrate the one end E1 of the supporter 110 and the other end E2 that is opposite to the one end E1. The supporter 110 may be formed in the shape of a barrel to prevent light irradiated by the light source unit 130 from leaking out, thereby concentrating the light on a target. Also, because a length of the supporter 110 ranging from the one end E1 to the other end E2 is fixed, it may be possible to maintain a constant distance from a target to the optical unit 115. The supporter 110 may contact the skin being a target at the other end E2. However, a skin condition may be measured in the state in which the supporter 110 is spaced from a target.

The sensor unit 120 may include a moisture sensor for measuring an amount of moisture in a target. Also, the sensor unit 120 may include an oil sensor for measuring an amount of oil in a target and a PH sensor for measuring a PH level of a target. The sensor unit 120 may measure a skin condition, an amount of moisture, an amount of oil, or a PH level of a target and generate a measurement signal. In this case, the skin diagnostic device 10 may further include a communication device (not shown) for allowing communication with the electronic device 20 as an external device to transmit the measurement signal to the electronic device 20.

The sensor unit 120 may be positioned on the other surface of the body 100, not on the one surface A1 of the body 100. The sensor unit 120 may be, as shown, positioned on an upper surface of the body 100 extending vertically to the one surface A1 of the body 100, so that a user photographs the skin through the image sensor 201 and then changes a measurement direction to measure an amount of moisture, etc. as a skin condition through the sensor unit 120. The sensor unit 120 may be positioned on the one surface A1 of the body 100 such that a measurement direction of the sensor unit 120 is parallel to that of the image sensor 201; however, a first imaginary line T1 passing the image sensor 201 and the optical unit 115 may cross a second imaginary line T2 passing a measurement surface of the sensor unit 120. In other words, a measurement direction of the image sensor 201 may be different from that of the sensor unit 120. In the skin diagnostic device 10 according to an embodiment, because the measurement direction of the image sensor 201 is different from that of the sensor unit 120, user convenience may increase.

Meanwhile, the skin diagnostic device 10 according to an embodiment may further include a power supply 180 for supplying power to the sensor unit 120 and the light source unit 130, and a switch 190 for enabling a user to turn the skin diagnostic device 10 on/off.

Referring to FIGS. 4 and 5, a coupling system for a skin diagnostic device according to an embodiment of the disclosure may include the skin diagnostic device 10, the electronic device 20, and the first coupling member 30. The skin diagnostic device 10 and the electronic device 20 have the above-described configurations, and therefore, for convenience of description, descriptions previously given will be omitted.

The first coupling member 30 may include a base 300, at least one magnetic body, and the first alignment member 305.

The base 300 may include a first surface B1 and a second surface B2 that is opposite to the first surface B1. The base 300 may have a predetermined shape on which the magnetic body is able to be arranged. The base 300 may be in the shape of a plate. On the first surface B1 of the base 300, the magnetic body may be arranged, and the base 300 may be coupled with the electronic device 20 through the second surface B2. According to an embodiment, the second surface B2 may include an adhesive material to be attached on the electronic device 20.

According to an embodiment, the magnetic body may include the third magnetic body 301 and the fourth magnetic body 303. The third magnetic body 301 may be positioned on the first surface B1 of the base 300 and have a first polarity. The fourth magnetic body 303 may have a second polarity that is different from the first polarity and be spaced from the third magnetic body 301 on the first surface B1. In this case, the third magnetic body 301 may be coupled with the first magnetic body 151 of the second coupling member 150, and the fourth magnetic body 303 may be coupled with the second magnetic body 153. Accordingly, the third magnetic body 301 may have an opposite polarity of that of the first magnetic body 151, and the fourth magnetic body 303 may have an opposite polarity of that of the second magnetic body 153. Also, a distance between the first magnetic body 151 and the second magnetic body 153 may be equal to a distance between the third magnetic body 301 and the fourth magnetic body 303. Herein, the distance means a distance between centers of two components. As described above, according to another embodiment, the magnetic body may include any one of the third magnetic body 301 and the fourth magnetic body 303.

Meanwhile, a distance between the first coupling member 30 and the image sensor 201 of the electronic device 20 may be equal to a distance between the second coupling member 150 and the optical unit 115. Accordingly, by coupling the first coupling member 30 with the second coupling member 150, the optical unit 115 of the skin diagnostic device 10 may be located precisely at the image sensor 201 of the electronic device 20.

Also, the first coupling member 30 may be aligned with the second alignment member 155 of the second coupling member 150, through the first alignment member 305 positioned adjacent to the magnetic body. In other words, when the first alignment member 305 includes a protrusion as shown in FIG. 4, the second alignment member 155 may include a groove corresponding to the protrusion to be inserted into the protrusion. A structure of the protrusion and the groove may firmly couple the first alignment member 305 with the second alignment member 155.

According to an embodiment, the first coupling member 30 may be coupled with the second coupling member 150 through the magnetic bodies that they include respectively. At this time, the first alignment member 305 may be aligned with the second alignment member 155 to be adjacent to the magnetic bodies, thereby further increasing position accuracy when the first coupling member 30 is coupled with the second coupling member 150. Accordingly, position accuracy of the image sensor 201 and the optical unit 115 may be more easily improved.

Referring to FIG. 6, according to another embodiment, the base 300 of the first coupling member 30 may be in the shape of a case that fits into the electronic device 20. When the base 300 is in the shape of a case, a distance between the first coupling member 30 and the image sensor 201 may be constant, which improves position accuracy of the skin diagnostic device 10 that is coupled with the first coupling member 30. In this case, the base 300 may have an opening 309 at a location corresponding to the image sensor 201 of the electronic device 20.

Meanwhile, although not shown, like the first coupling member 30, the second coupling member 150 may also be in the shape of a case that fits into the skin diagnostic device 10. The second coupling member 150 may include a third surface that is opposite to the first surface B1 of the first coupling member 30, and a fourth surface that is opposite to the third surface. In this case, the third and fourth surfaces of the second coupling member 150 may be in the shape of a case. When the second coupling member 150 is in the shape of a case, an opening may be formed at a location corresponding to the optical unit 115 so that the optical unit 115 may be exposed to the outside.

Figure 7:
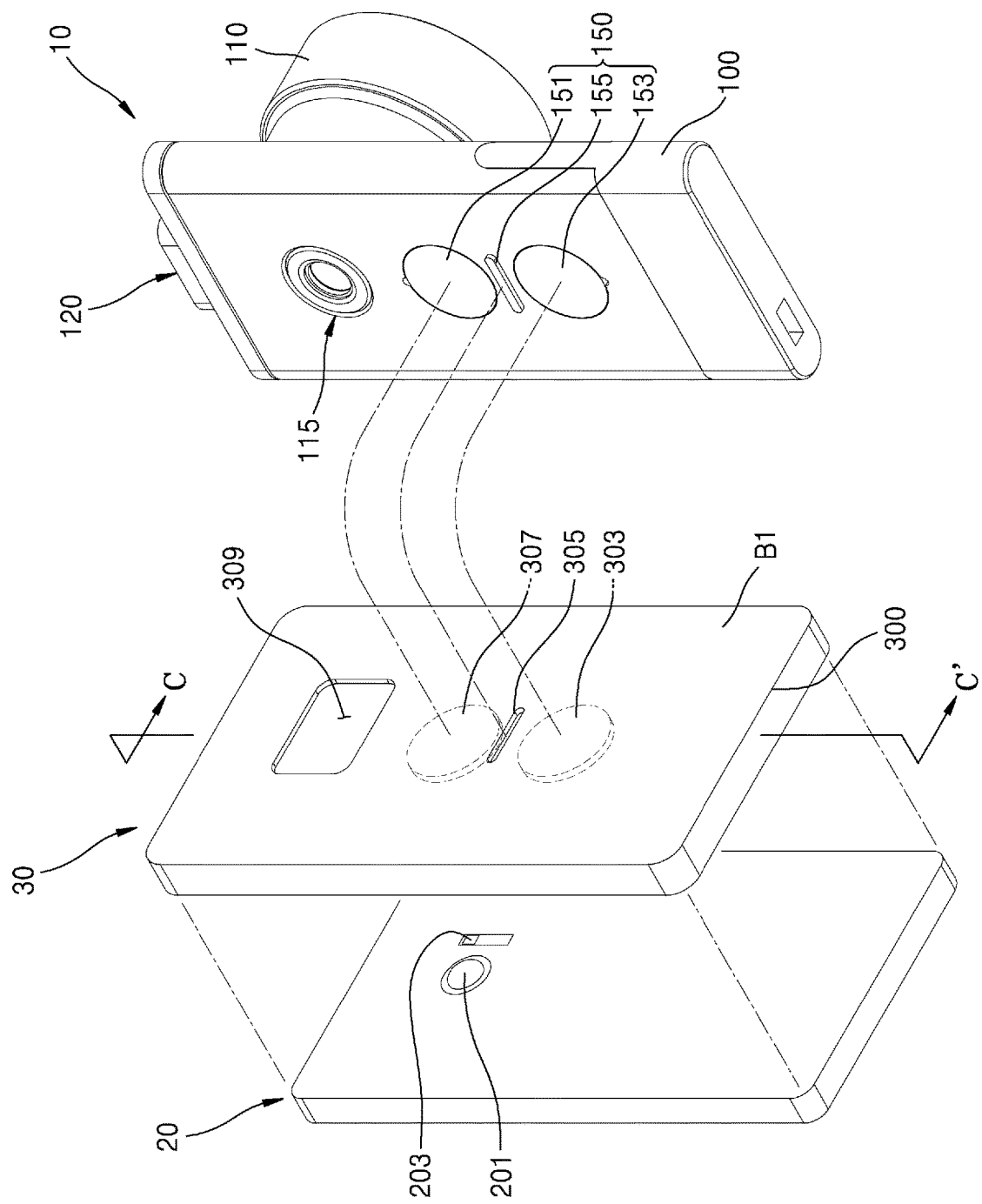
FIG. 7 shows another embodiment in which the skin diagnostic device shown in FIG. 4 is coupled with an electronic device.
Figure 8:
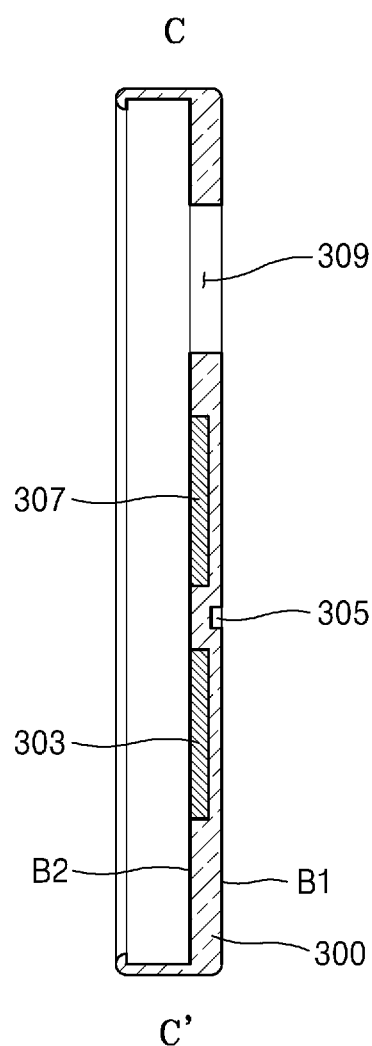
FIG. 8 is a cross-sectional view of the embodiment shown in FIG. 7, taken along line C-C'.

FIG. 7 shows another embodiment in which the skin diagnostic device 10 shown in FIG. 4 is coupled with the electronic device 20, and FIG. 8 is a cross-sectional view of the embodiment shown in FIG. 7, taken along line C-C'.

Referring to FIGS. 7 and 8, the base 300 may include the first surface B1 and the second surface B2 that is opposite to the first surface B1. The base 300 may have a predetermined shape on which the magnetic body is able to be arranged, and the base 300 may be in the shape of a case, as shown. The base 300 may be coupled with the electronic device 20 through the second surface B1, and the magnetic body may be arranged on the second surface B1. Because the magnetic body is arranged on the second surface B2 on which the first coupling member 30 is coupled with the electronic device 20, the magnetic body may not be exposed to the outside. In the first coupling member 30, a concave portion may be formed toward the inside of the base 300 from the second surface B2, and the magnetic body may be positioned in the concave portion. One surface of the magnetic body may be co-planar with the second surface B2 of the base 300. Also, a thickness from the other surface of the magnetic body that is opposite to the one surface of the magnetic body to the first surface B1 may be a thickness at which a magnetic force of the magnetic body is able to be transmitted to the outside.

In this case, the first coupling member 30 may include the third magnetic body 301 and the fourth magnetic body 303, and include the first alignment member 305 positioned between the third magnetic body 301 and the fourth magnetic body 303. According to an embodiment, the first alignment member 305 may include a long, straight-lined groove, as shown, and the second alignment member 155 corresponding to the first alignment member 305 may include a protrusion corresponding to the groove to be inserted into the groove. The first coupling member 30 may arrange the magnetic body in the inside and include the first alignment member 305 in the shape of a groove, thereby improving an esthetic sense in external appearance and maximizing convenience of use.

Figure 9:
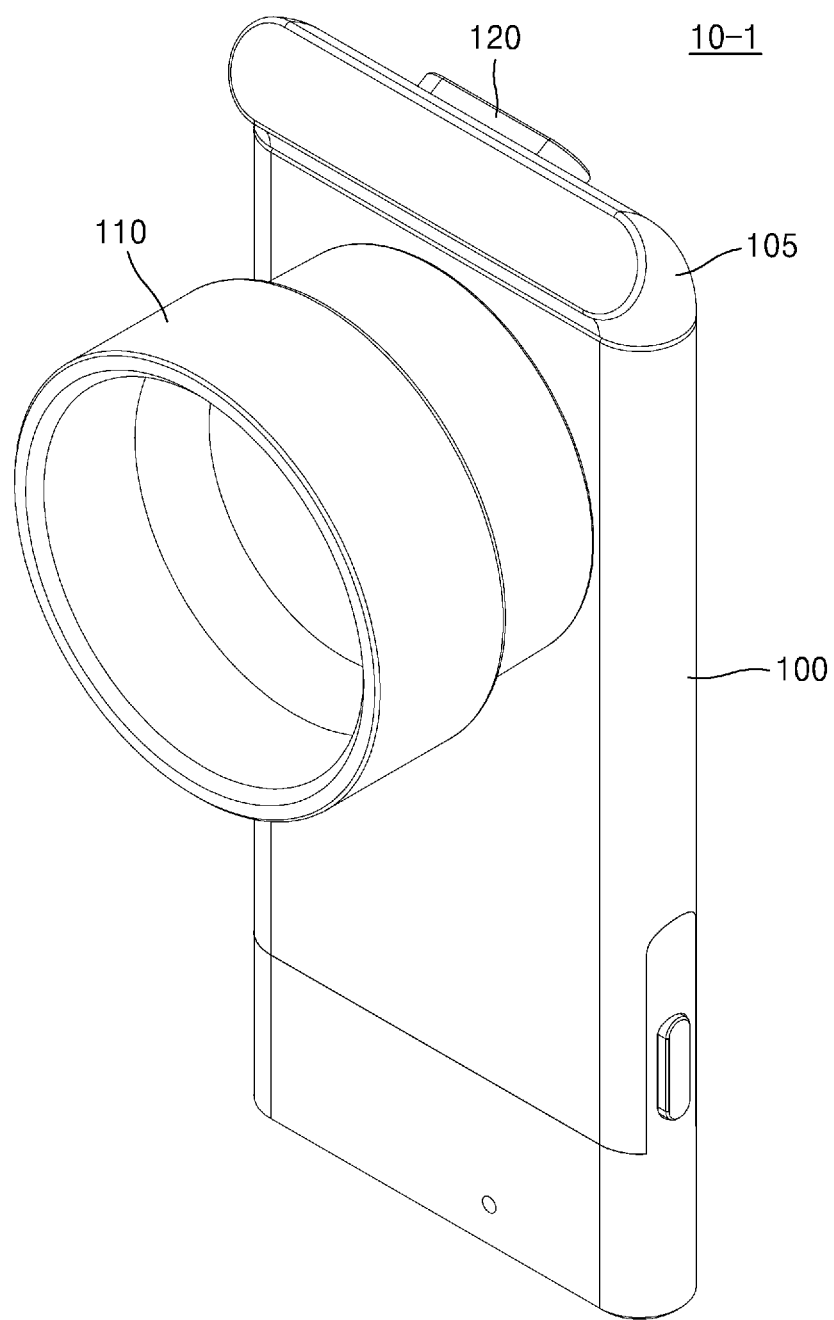
FIG. 9 is a perspective view of a skin diagnostic device according to another embodiment of the disclosure.
Figure 10:
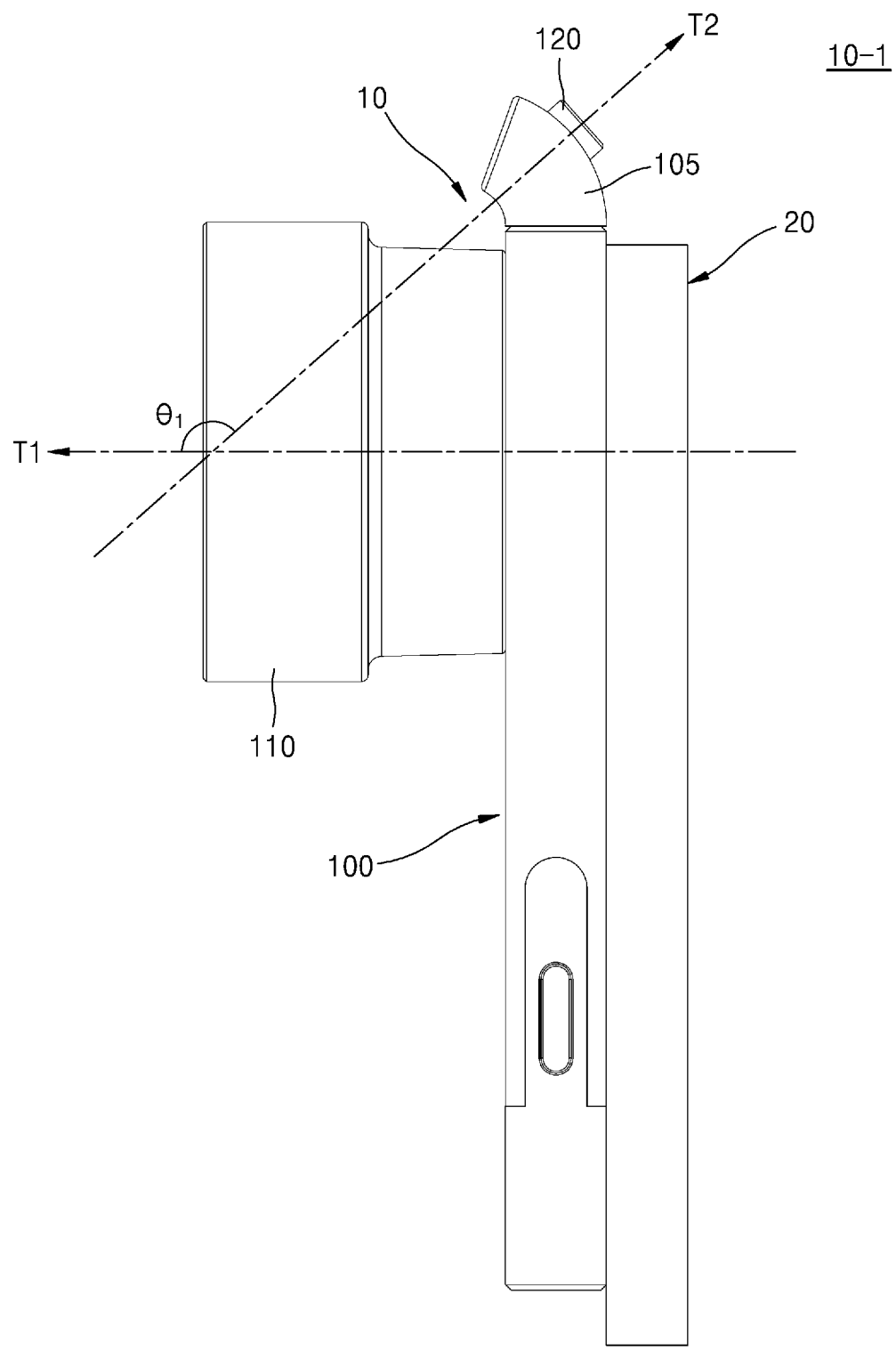
FIG. 10 is a side view of the skin diagnostic device shown in FIG. 9.

FIG. 9 is a perspective view of a skin diagnostic device 10-1 according to another embodiment of the disclosure, and FIG. 10 is a side view of the skin diagnostic device 10-1 shown in FIG. 9.

Referring to FIGS. 9 and 10, the skin diagnostic device 10-1 according to another embodiment of the disclosure may include the body 100, the optical unit 115, the sensor unit 120, the supporter 110, and an extension portion 105. Components of the skin diagnostic device 10-1 according to the other embodiment are the same as those of the one embodiment, except for the extension portion 105, and therefore, descriptions previously given will be omitted.

The extension portion 105 may extend from the one surface A1 of the body 100 and include an extension surface inclined with respect to the one surface A1. In this case, the extension surface may be an inclined surface, or a curved surface as shown. According to an embodiment, the extension portion 105 may be connected to the one surface A1 and positioned on the other surface being adjacent to the optical unit 115.

The sensor unit 120 may be positioned on the extension portion 105. The sensor unit 120 may include a moisture sensor for measuring an amount of moisture in a target. Also, the sensor unit 120 may further include an oil sensor and a PH sensor. The sensor unit 120 may have a measurement direction that is different from the measurement direction of the image sensor 201, as shown. Particularly, because the sensor unit 120 is positioned on the extension portion 105 inclined and extending from the body 100 in the skin diagnostic device 10-1 according to another embodiment, a user may more conveniently use the sensor unit 120 for measurement. The first imaginary line T1 passing the image sensor 201 and the optical unit 115 may cross the second imaginary line T2 passing a measurement surface of the sensor unit 120. For example, an angle θ2 between the first imaginary line T1 and the second imaginary line T2 may form an obtuse angle with respect to the measurement directions.

Figure 11:
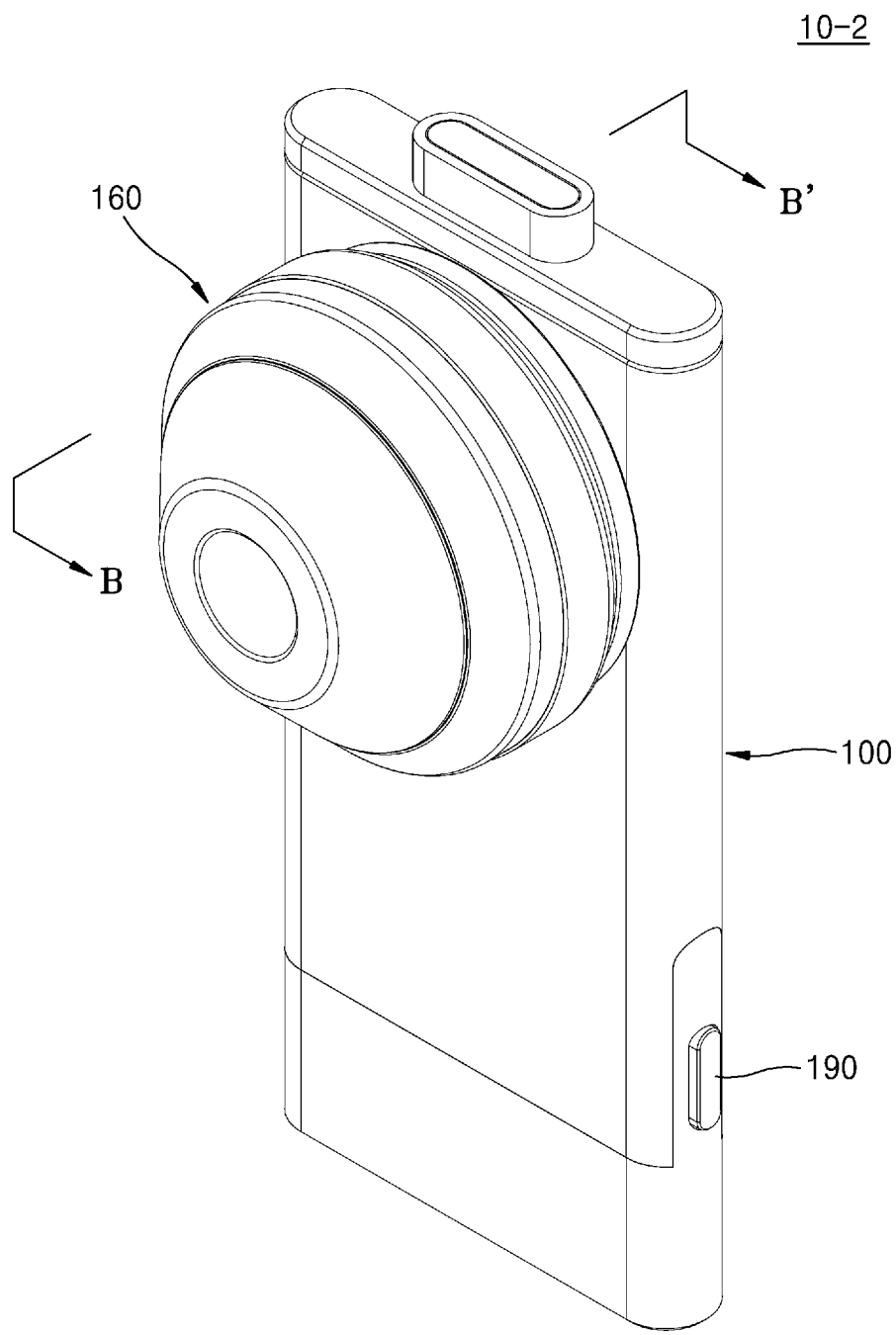
FIG. 11 is a perspective view of a skin diagnostic device according to another embodiment of the disclosure.
Figure 12:
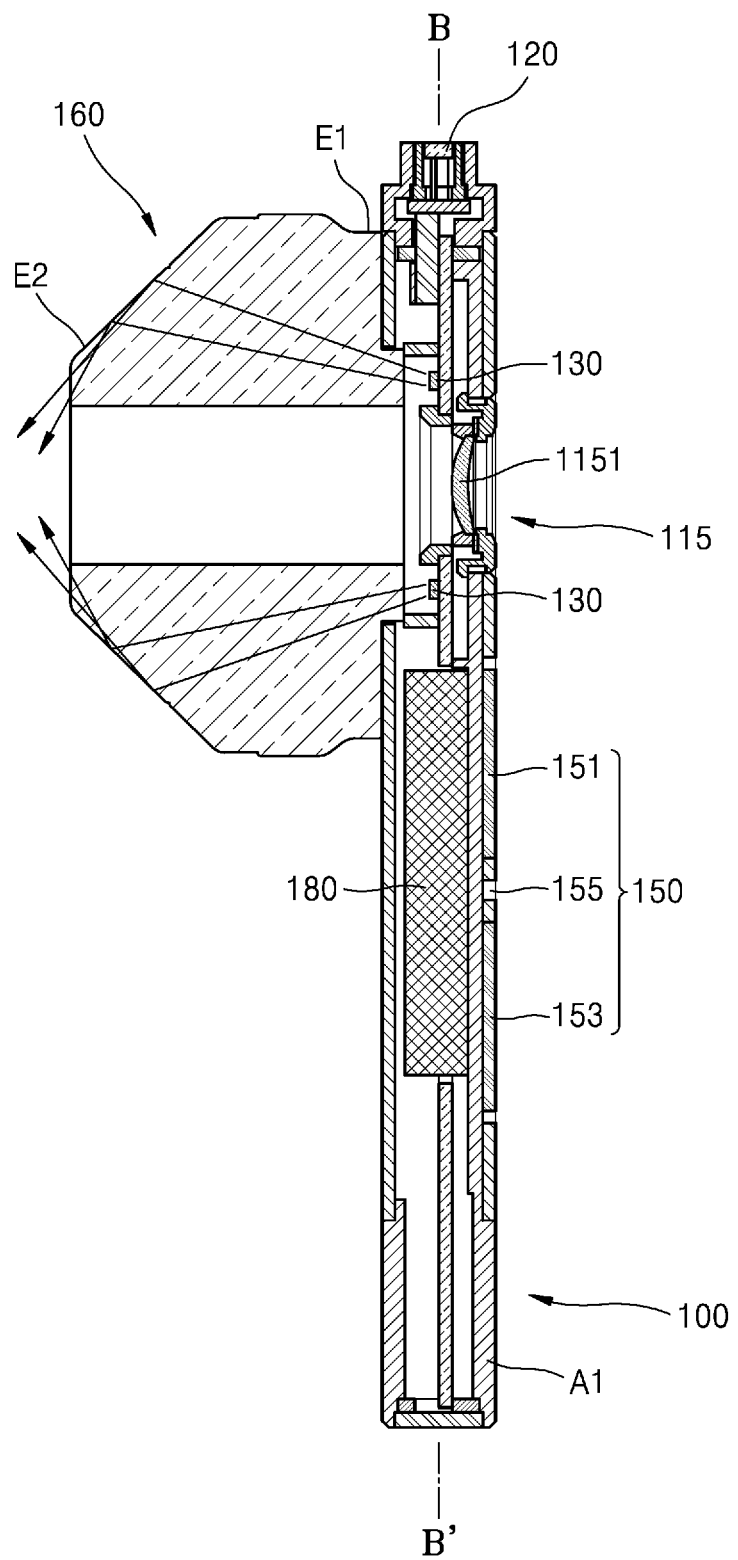
FIG. 12 is a cross-sectional view of the skin diagnostic device shown in FIG. 11, taken along line B-B'.

FIG. 11 is a perspective view of a skin diagnostic device 10-2 according to another embodiment of the disclosure, and FIG. 12 is a cross-sectional view of the skin diagnostic device 10-2 shown in FIG. 11, taken along line B-B'.

Referring to FIGS. 11 and 12, components of the skin diagnostic device 10-2 according to another embodiment of the disclosure are the same as those of the one embodiment, except for a second supporter 160, and therefore, descriptions previously given will be omitted.

One end E1 of the second supporter 160 may be positioned on the other surface of the body 100, the other surface being opposite to the one surface A1 of the body 100, and an opening penetrating the one end E1 and the other end E2 that is opposite to the one end E1 may formed. The second supporter 160 may be attached/detached to/from the body 100 through the one end E1.

Meanwhile, the second supporter 160 may further include a light guide member positioned on a path of light irradiated from the light source unit 130. According to an embodiment, the remaining portion of the second supporter 160 except for the opening may be the light guide member. The light guide member may receive light from the light source unit 130 through the one end E1. The light guide member may include, for example, a prism. The light guide member may change a path of light entering from the light source unit 130 to focus the light toward the other end of the second supporter 160. At least one part of light irradiated from the light source unit 130 may be diffused. The light guide member including a prism may reflect or refract the diffused light to thereby change a path of the light to focus the light at the other end of the second supporter 160. Thus, the skin diagnostic device 10-2 may concentrate light on a surface of a target, that is, the skin, to obtain a more precise image.

As described above, because the skin diagnostic device according to the embodiments of the disclosure is coupled with the electronic device by using the coupling members including the magnetic bodies with different polarities, the optical unit of the skin diagnostic device may be located precisely at the image sensor of the electronic device. Therefore, a user may measure a skin condition under the same condition at any time so that an accurate skin diagnosis may be possible.

Also, because the skin diagnostic device according to the embodiments of the disclosure further includes the sensor unit for measuring an amount of moisture in the skin, the skin diagnostic device may acquire more information for a skin diagnosis. Particularly, because the measurement direction of the sensor unit is different from the measurement direction of the image sensor in the skin diagnostic device, a user may more conveniently use the sensor unit to measure the skin.

Also, because the skin diagnostic device according to the embodiments of the disclosure further includes the light guide member for focusing light entering from the light source unit on the skin, the skin diagnostic device may acquire a clear, accurate skin measurement image.

Up to this point, preferred embodiments of the disclosure have been described with reference to the accompanying drawings. It will be apparent that those skilled in the art may readily make various modifications thereto without changing the essential features of the disclosure. Thus, it should be understood that the disclosed embodiments described above are merely for illustrative purposes and not for limitation purposes in all aspects. The scope of the disclosure is defined in the accompanying claims rather than the above detailed description, and it should be noted that all differences falling within the claims and equivalents thereof are included in the scope of the disclosure.

INDUSTRIAL APPLICABILITY

According to an embodiment of the disclosure, there is provided a skin diagnostic device that is removably coupled with a portable electronic device. Also, the embodiments of the disclosure are applicable to a removable portable diagnosis device used in industrial fields.

What is claimed is:

1. A skin diagnostic device comprising:
a body comprising a coupling member positioned on a first surface, the body being attached/detached to/from an electronic device including an image sensor by using the coupling member;
an optical unit positioned in the body and comprising at least one lens, wherein the optical unit is configured to focus measurement light reflected from a target on the image sensor of the electronic device; and
at least one light source unit positioned adjacent to the optical unit and configured to irradiate light toward the target,
wherein the coupling member comprises a first magnetic body and a second magnetic body and an alignment member positioned between the first magnetic body and the second magnetic body and extending in length between the first magnetic body and the second magnetic body;
wherein the first magnetic body, the alignment member, and the second magnetic body are positioned on a same line as the optical unit; and
wherein the alignment member extends in length in a second direction perpendicular to a first direction in which the same line extends.

2. The skin diagnostic device of claim 1, further comprising:
a sensor unit positioned on a second surface of the body, the sensor unit comprising a moisture sensor configured to measure an amount of moisture in the target.

3. The skin diagnostic device of claim 1, further comprising:
a sensor unit comprising a moisture sensor configured to measure an amount of moisture in the target,
wherein a first imaginary line passing the image sensor and the optical unit crosses a second imaginary line passing a measurement surface of the sensor unit.

4. The skin diagnostic device of claim 1, further comprising:
a supporter including a first end positioned on a second surface of the body, where the second surface is opposite to the first surface of the body, and wherein an opening penetrating the first end and a second end that is opposite to the first end is formed in the supporter.

5. The skin diagnostic device of claim 4, wherein:
the supporter further comprises a light guide member positioned on a path of light irradiated from the at least one light source unit and configured to change a path of at least one part of the light irradiated from the at least one light source unit to focus the light on the second end of the supporter.

6. The skin diagnostic device of claim 1, wherein:
the at least one light source unit comprises a plurality of light sources spaced at regular intervals while surrounding the optical unit.

7. A coupling system for a skin diagnostic device, comprising:
a first coupling member comprising a first surface and a second surface that is opposite to the first surface, the first coupling member comprising a first magnetic body and a second magnetic body positioned on the first surface and a first alignment member positioned between the first magnetic body and the second magnetic body and extending in length between the first magnetic body and the second magnetic body;
a second coupling member comprising a third surface that is opposite to the first surface and a fourth surface that is opposite to the third surface, the second coupling member comprising a third magnetic body and a fourth magnetic body positioned on the third surface and a second alignment member positioned between the third magnetic body and the fourth magnetic body and aligned with the first alignment member;

an electronic device comprising the first coupling member and an image sensor; and a skin diagnostic device comprising:
- a body comprising the second coupling member positioned on one surface thereof, the body being attached/detached to/from the electronic device using the second coupling member;
- an optical unit positioned in the body and comprising at least one lens, the optical unit being configured to focus measurement light reflected from a target on the image sensor of the electronic device; and
- at least one light source unit positioned adjacent to the optical unit and configured to irradiate light toward the target;

wherein the third magnetic body, the second alignment member, and the fourth magnetic body of the second coupling member is positioned on a same line as the optical unit, and the second alignment member extends in length in a second direction perpendicular to a first direction in which the same line extends.

8. The coupling system of claim 7, wherein the skin diagnostic device further comprises:
- a sensor unit positioned on a second surface of the body, the sensor unit comprising a moisture sensor configured to measure an amount of moisture in the target.

9. The coupling system of claim 7, wherein:
- the skin diagnostic device further comprises a sensor unit including a moisture sensor configured to measure an amount of moisture in the target,
- wherein a first imaginary line passing the image sensor and the optical unit crosses a second imaginary line passing a measurement surface of the sensor unit.

10. The coupling system of claim 7, wherein the skin diagnostic device further comprises:
- a supporter including a first end positioned on the second surface of the body, the second surface being opposite to the first surface of the body, wherein an opening penetrating the first end and a second end being opposite to the first end is formed in the supporter.

11. The coupling system of claim 10, wherein:
- the supporter further comprises a light guide member positioned on a path of light irradiated from the at least one light source unit and configured to change a path of at least one part of the light irradiated from the at least one light source unit to focus the light on the other end of the supporter.

\* \* \* \* \*